United States Patent [19]
Martin

[11] Patent Number: 5,976,103
[45] Date of Patent: *Nov. 2, 1999

[54] DUAL LUMEN COAXIAL CATHETER

[75] Inventor: Geoffrey S. Martin, Mississauga, Canada

[73] Assignee: Vas-Cath Incorporated, Mississauga, Canada

[*] Notice: This patent is subject to a terminal disclaimer.

[21] Appl. No.: 08/880,601

[22] Filed: Jun. 23, 1997

Related U.S. Application Data

[63] Continuation of application No. 08/507,880, Jul. 27, 1995, abandoned, which is a continuation of application No. 08/209,859, Mar. 14, 1994, abandoned, which is a continuation of application No. 07/834,750, Feb. 13, 1992, abandoned.

[30] Foreign Application Priority Data

Sep. 26, 1991 [CA] Canada ................................. 2052300

[51] Int. Cl.$^6$ ..................................................... A61M 3/30
[52] U.S. Cl. ................................ 604/43; 604/35; 604/284
[58] Field of Search ................................. 604/43, 27, 35, 604/39, 173, 283, 280, 284, 165

[56] References Cited

U.S. PATENT DOCUMENTS

| Re. 31,873 | 4/1985 | Howes . |
| 206,074 | 7/1878 | Beckwith . |
| D. 272,651 | 2/1984 | Mahurkar . |
| 298,303 | 5/1884 | Krementz . |
| 1,777,120 | 9/1930 | Lewin . |
| 1,800,839 | 4/1931 | Lewin . |
| 4,037,599 | 7/1977 | Raulerson ............................ 128/214.4 |
| 4,072,146 | 2/1978 | Howes . |
| 4,096,860 | 6/1978 | McLaughlin ........................ 128/214.4 |
| 4,134,402 | 1/1979 | Mahurkar . |
| 4,203,436 | 5/1980 | Grimsrud . |
| 4,217,895 | 8/1980 | Sagae et al. . |
| 4,274,417 | 6/1981 | Delpy . |
| 4,352,354 | 10/1982 | Ujihara . |
| 4,385,631 | 5/1983 | Uthmann .................................. 604/43 |
| 4,411,055 | 10/1983 | Simpson et al. .......................... 29/447 |
| 4,493,696 | 1/1985 | Uldall ...................................... 604/43 |
| 4,643,711 | 2/1987 | Bates . |
| 4,666,426 | 5/1987 | Aigner ...................................... 604/5 |
| 4,692,141 | 9/1987 | Mahurkar . |
| 4,722,725 | 2/1988 | Sawyer et al. ............................ 604/27 |

(List continued on next page.)

FOREIGN PATENT DOCUMENTS

| 0025704 | 3/1981 | European Pat. Off. ........ A61M 25/00 |
| 25704 | 3/1981 | European Pat. Off. . |
| 0333308 | 9/1989 | European Pat. Off. ........ A61M 25/00 |
| 333308 | 9/1989 | European Pat. Off. . |
| 1014570 | 3/1964 | United Kingdom . |
| 2130093 | 5/1984 | United Kingdom . |

OTHER PUBLICATIONS

Kementz v.S. Cottle Co., 148 U.S. 156 (1892).
Howard v. Detroit Stove Works, 150 U.S. 164 (1893).
Pyle National Co., v. Lewin, 92 F.2d 628 (7th Cir. 1973).

Primary Examiner—Wynn Wood Coggins
Assistant Examiner—A. T. Nguyen
Attorney, Agent, or Firm—Trask, Britt & Rossa

[57] ABSTRACT

A dual lumen catheter is provided having an elongate body defining coaxial intake and return lumens and a junction containing a proximal end of the body with parts of the lumens in the junction constrained in side-by-side relationship. First and second connecting tubes are engaged in the junction and extend generally longitudinally away from the main body. The junction provides fluid continuity between the first connecting tube and the intake lumen and between the second connecting tube and the return lumen to permit the catheter to be used for simultaneous dual flow. The distal end of the catheter includes a conical transition portion at which the exterior diameter of the dual lumen main catheter section is smoothly reduced to that of an open-ended, single lumen cylindrical tip section of lesser diameter.

20 Claims, 3 Drawing Sheets

U.S. PATENT DOCUMENTS

| | | | |
|---|---|---|---|
| 4,772,268 | 9/1988 | Bates . | |
| 4,776,841 | 10/1988 | Catalano . | |
| 4,808,155 | 2/1989 | Mahurkar . | |
| 4,895,561 | 1/1990 | Mahurkar | 604/43 |
| 4,961,809 | 10/1990 | Martin | 604/43 |
| 4,968,307 | 11/1990 | Dake et al. | 604/264 |
| 5,053,004 | 10/1991 | Markel et al. | 604/43 |
| 5,106,368 | 4/1992 | Uldall et al. | 604/43 |
| 5,135,599 | 8/1992 | Martin et al. | 156/294 |
| 5,167,623 | 12/1992 | Cianci et al. | 604/43 |
| 5,207,648 | 5/1993 | Gross | 604/164 |
| 5,350,358 | 9/1994 | Martin | 604/43 |
| 5,360,397 | 11/1994 | Pinchuk | 604/27 |
| 5,380,276 | 1/1995 | Miller et al. . | |
| 5,478,331 | 12/1995 | Heflin et al. | 604/283 |
| 5,480,380 | 1/1996 | Martin | 604/43 |
| 5,568,329 | 10/1996 | Mahurkar . | |

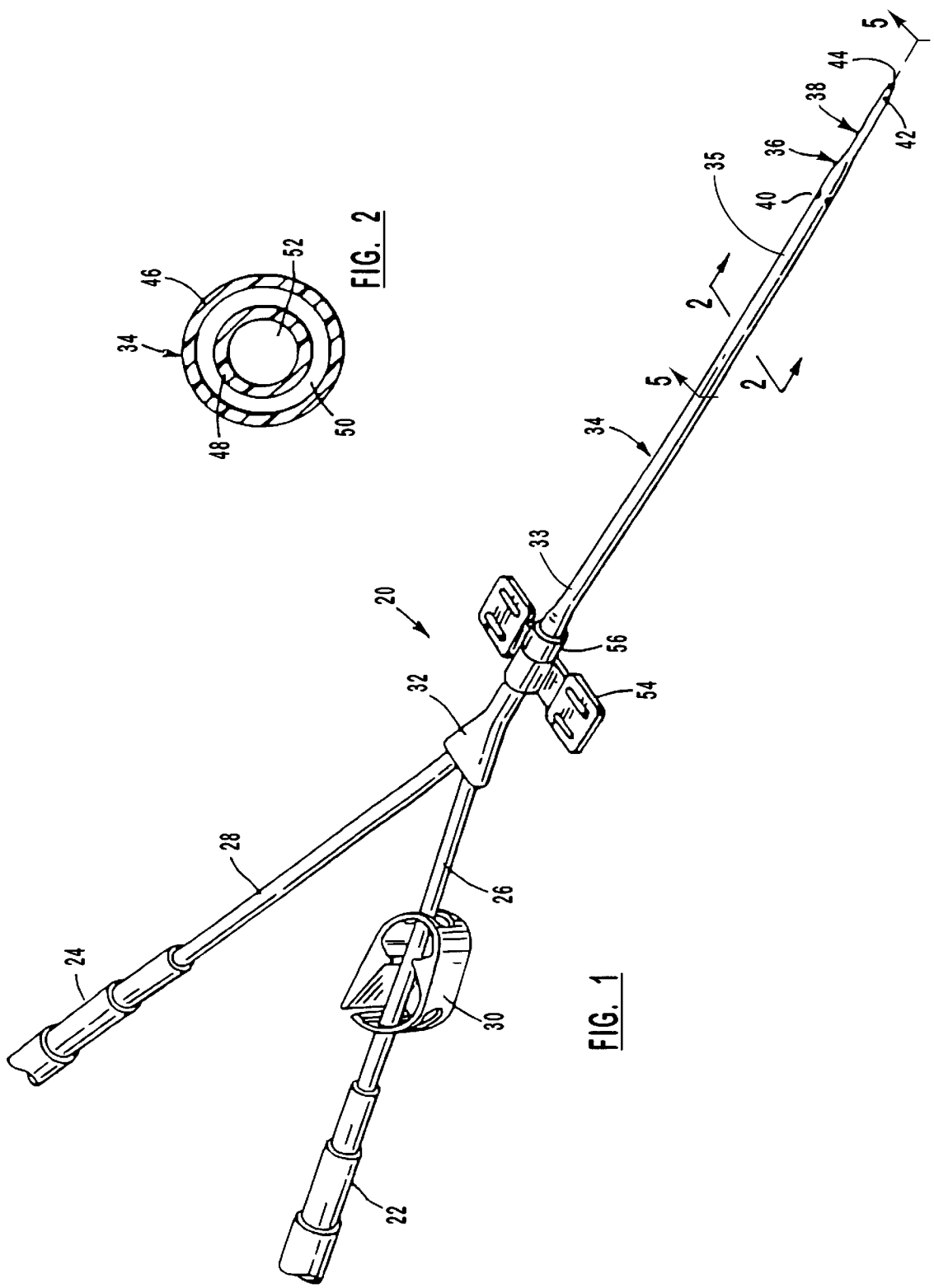

DUAL LUMEN COAXIAL CATHETER

RELATED APPLICATIONS

This application is a continuation application of U.S. patent application Ser. No. 507,880 that was filed on Jul. 27, 1995, abandoned, which was a continuation application of now abandoned U.S. patent application Ser. No. 209,859 filed on Mar. 14, 1994, which is a continuation application of U.S. patent application Ser. No. 834,750 filed on Feb. 13, 1992 abandoned.

FIELD OF THE INVENTION

This invention relates to dual lumen catheters for use in hemodialysis treatments and more particularly to a dual lumen catheter having coaxial intake and return lumens.

BACKGROUND OF THE INVENTION

Hemodialysis treatments have been developed since the early 1960s using a variety of combinations and arrangements of catheters. The earliest treatments were conducted using two needles in the same vein, and this subsequently led to pioneer work done by Dr. Shaldon in England who used two flexible catheters which could be left in place for limited periods. It was recognized by some practitioners that it would be preferable to use a single incision rather than to use two incisions and this led to the development of techniques involving dual flow catheters. There are two basic types. The first to be attempted was a coaxial catheter with the intake lumen surrounding the return lumen. While this had advantages, there were some difficulties of manufacture. The other approach is to use side-by-side lumens either in individual tubes connected to one another or in a single tube divided by an interior septum so that the lumens are D-shaped. These structures also had advantages and disadvantages, the notable disadvantages being that because the lumens are side-by-side, the intake openings must be in one side of the catheter. As a consequence of this, if the catheter were to attach itself to the wall of a vein due to suction applied to the intake lumen, then the flow would stop. Medical staff then have to move the catheter by rotating it until blood again flows. This is a very delicate manipulation which is normally performed only by a qualified medical practitioner who must be available at all times in case the flow is discontinued.

The side-by-side structures have advantages in manufacture due to the fact that the two lumens can be created simultaneously in an extrusion. This has led to great activity in developing devices having side-by-side D-shaped lumens at the expense of coaxial structures. Nevertheless, due to the inherent disadvantages of the side-by-side structures, there has been renewed interest in developing suitable coaxial devices. This is primarily because the intake lumen can have openings in any part of the wall of the catheter. As a result, no matter where the catheter may rest against a vein, some of the intake openings remain patent. There is then less likelihood that the procedures must be serviced by a trained medical practitioner.

An early patent showing the use of coaxial tubing in haemodialysis treatments is U.S. Pat. No. 4,037,599 to Raulerson. This structure involves the use of a needle forming the return lumen and a coaxial sleeve which is tapered at its leading end to follow the incision made by the needle and to provide an intake lumen between the tube and the needle. This structure can not of course be left in place, but it is an indication of the approach to the use of coaxial tubes to form two lumens.

Another structure involving the use of a needle is found in U.S. Pat. No. 4,073,297 to Kopp. Again this structure involves a tube about a needle to define an intake lumen and blood is returned through the needle.

A further approach to co-axial dual lumens is found in U.S. Pat. No. 4,196,860 to McLaughlin. In this structure the intake lumen is open at its end, and blood is withdrawn down this lumen about the return lumen. Further structures of a similar kind are to be found in U.S. Pat. No. 4,202,332 to Tersteegen et al.

U.K. Patent Application No. GB 2017499 A teaches the use of a dual lumen coaxial catheter made of flexible plastics material. The inner tube projects beyond the outer tube to form a return lumen, and the intake lumen is tapered at its end to close about the return lumen. This kind of structure is also to be found in Canadian Patent 1,150,122 to the present inventor.

A contrasting structure is shown in U.S. Pat. No. 4,493,696 to Uldall. In this the outer tube converges to fit about the inner tube and then projects beyond the inner tube to form an extension of the inner tube at the tip. Although this contrasts with all of the previous structures mentioned, there are disadvantages in this arrangement. Notably that there is a discontinuity where the end of the inner tube terminates, and the rigidity of the tip is determined by the material of the outer tube, which of course must be sufficiently rigid to maintain its patency in use.

Another reference known to applicant and involving a coaxial dual lumen arrangement is found in U.S. Pat. No. 4,666,426 to Aigner, which uses the inner tube to form a tip.

These prior art structures suffer from contrasting design criteria which have the effect of limiting the acceptance of coaxial dual lumen catheters in hemodialysis. In all instances the tip section is made up of material formed from an extension of either the inner or outer tubes forming the dual flow portion of the catheter. As a result the tip section has the same physical characteristics as parts chosen to be sufficiently stiff to resist kinking, if the catheter should be bent. By contrast, it is desirable that the tip section be sufficiently soft and pliable to permit this section to take up the local shape of a vein containing the catheter, thereby to avoid applying distorting forces to the vein and to permit prolonged access with a suitable selection of materials.

SUMMARY OF THE INVENTION

It is among the objects of the present invention to provide an improved dual lumen coaxial catheter.

Accordingly, in one of its aspects the invention provides a dual lumen catheter having an elongate body defining coaxial intake and return lumens and a junction containing a proximal end of the body with parts of the lumens in the junction constrained in side-by-side relationship. First and second connecting tubes are engaged in the junction and extend generally longitudinally away from the main body. The junction provides fluid continuity between the first connecting tube and the intake lumen and between the second connecting tube and the return lumen thereby to permit the catheter to be used for simultaneous dual flow.

BRIEF DESCRIPTION OF THE DRAWINGS

The invention will be better understood with reference to the drawings and the following description, in which:

FIG. 1 is an isometric view of a catheter according to one embodiment of the invention;

FIG. 2 is a cross-sectional view of FIG. 1 taken along section 2—2 shown therein and drawn to a larger scale;

DESCRIPTION OF PREFERRED EMBODIMENTS OF THE INVENTION

Figure 3:
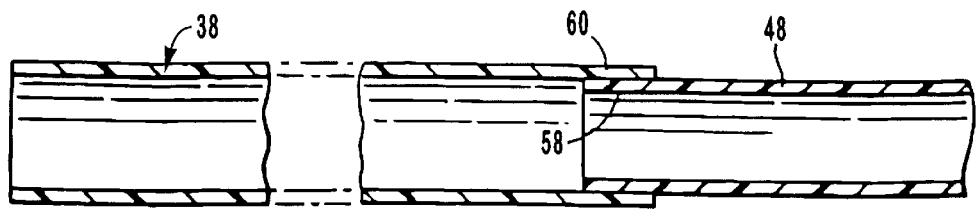
FIGS. 3 and 4 illustrate steps in the procedure of manufacturing the distal end of the catheter of FIG. 1.

FIG. 1 illustrates a catheter 20 useful for withdrawing blood through an intake fitting 22 and returning treated blood through an outlet fitting 24. Intake fitting 22 and outlet fitting 24 are connected to the proximal ends of flexible access tubes 26, 28, respectively, which can be closed selectively to fluid flow using conventional devices, such as a clamp 30 shown on access tube 26. Access tubes 26, 28 meet at a junction 32 located at the proximal end 33 of a main catheter section 34. The distal end 35 of main catheter section 34 terminates in a transition portion 36 from which projects a tip section 38 of reduced outer diameter relative to that of main catheter section 34. Blood is withdrawn through a set of first side openings 40, and blood returns through a set of second side openings 42 and an end opening 44.

As seen in FIG. 2, main catheter section 34 includes an outer tube 46 that encircle an inner tube 48. First openings 40, shown in FIG. 1, supply blood to an intake lumen 50 formed between the tubes 46, 48 and blood returns by a return lumen 52 contained within the inner tube 48. The junction 32 at the proximal end 33 of the main section 34 connects the main catheter section to the access tubes 26, 28 (as will be explained), and the catheter 20 is completed by provision of a wing structure 54 used to attach the catheter in place in conventional fashion. It is preferable that the wing structure 54 be rotatable on the catheter 20 and provision is made for this by a sleeve 56 which prevents movement of the wing structure 54 longitudinally relative to the catheter 20.

The side openings 40 and 42 are typical of openings that can be provided around the periphery of a catheter to ensure flow into and out of the catheter from anywhere about the catheter 20. Consequently, if the catheter should be positioned so that some of the openings 40 and 42 are occluded by positioning against the wall of a vein, other of openings 40 and 42 will take over and provide the essential flow.

Reference is next made to FIG. 3 to illustrate a preliminary step in the manufacture of the catheter 20. As seen in FIG. 3, inner tube 48 has a leading distal part 58 that is disposed within a corresponding part 60 of the tip section 38. These respective leading parts can of course be deformed to fit together in this way, but as shown the round tubing is selected for these parts so that they fit within one another quite readily but at the same time quite closely. If preferred, the parts can be attached to one another using a suitable adhesive. Typically the inner tube is 6 French and the tip section 8 French. (French is a scale of sizes used in the art, one French being about 0.013 inches).

Figure 4:
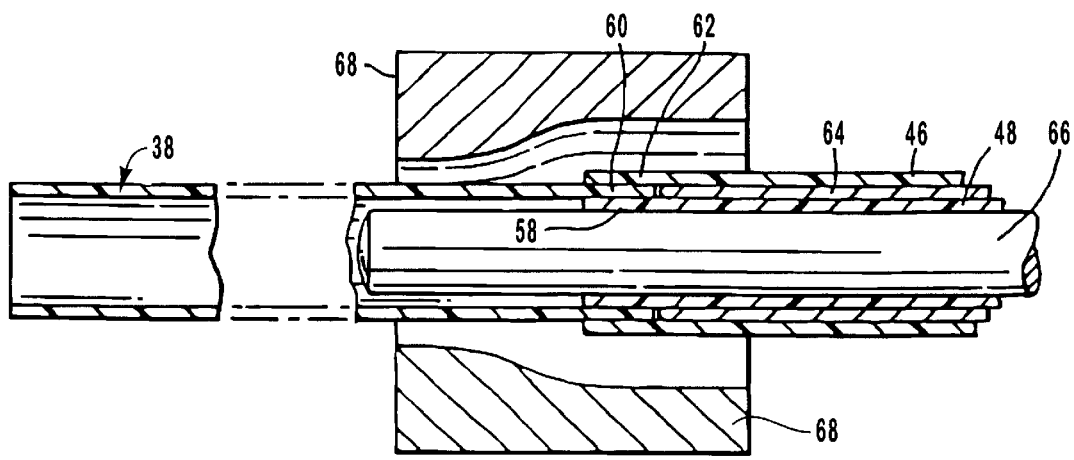

An assembly is then created as shown in FIG. 4. There it will be seen that the outer tube 46 is now in place about the inner tube 48 and a leading distal part 62 of the outer tube 46 overlaps leading proximal part 60 of the tip section 38. Consequently the leading parts 58, 60 and 62 are overlapped and located about one another, and again an adhesive can be used to fix the assembly.

A tubular cylindrical mandrel 64 is proportioned to fit inside the outer tube 46 and about the inner tube 48. Typically the outer tube 48 is 12 French, and the materials of all of the inner and outer tubes 48, 46, respectively, and the tip section 38 are polyurethane, with the selection of the materials being chosen to give the physical characteristics desired. For instance, if a soft tip structure is required, then a material of a suitable Durometer is provided for the tip section 38. Sufficient rigidity must be provided, however, in inner tube 48 and outer tube 46, to ensure against collapse under any reasonable curvature needed to implant catheter 20 completely in the body of a patient. It should be noted that the inner tube 48 is protected to some extent against collapse by the outer tube 46 so that the inner tube 48 can be of a relatively thin wall. This maximizes the space available for flow in the catheter 20.

A solid second mandrel 66 is provided to support the inner tube 46 so that this tube extends between the mandrels 64 and 66. Mandrel 64 has a rounded end and stops against the leading proximal part 60 of the tip section 38, whereas the inner mandrel 66 projects into the tip section 38. This provides support along a space to be occupied by two halves of a mold 68 which illustrated in FIG. 4 that are operable to finish the assembly shown in FIG. 4 into a structure, such as transition portion 36 shown in FIG. 1.

The mold 68 is used to form the transition portion 36 by moving the mold halves into contact with the assembly shown in FIG. 4. Under the influence of sufficient heat, the pressure of the halves of mold 68 causes the material of leading parts 58, 60, and 62 to flow together. Once this is completed, the structure is allowed to cool, and the mandrels 64, 66 removed. The result is shown in FIG. 5.

Figure 5:
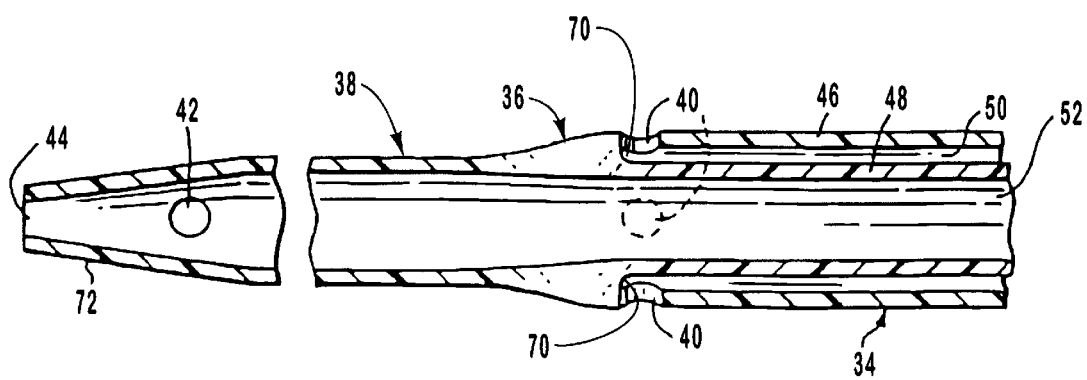
FIG. 5 is a cross-sectional view taken along section 5—5 of FIG. 1 and showing the distal end of the catheter to a larger scale.

As seen in FIG. 5, the intake lumen 50 terminates at a blind annular end wall 70 at the transition portion 36. The intake lumen 50 is contained between outer tube 46 and inner tube 48, and the first side openings 40 are provided immediately adjacent the transition portion 36 to allow blood flow into intake lumen 50. More of such openings 50 can be provided further away from the transition portion 36 if required.

The return lumen 52 is formed by the inner tube 48, the transition portion 36, and the tip section 38. The transition portion 36 ends the intake lumen 50 and blends smoothly from the outer surface of the tip section 38 to the outer surface of the main catheter section 34, and in particular to the outer surface of the outer tube 46.

It should be noted in FIG. 5 that the three parts, namely the outer and inner tubes 46, 48 and the tip section 38, are shown as three individual parts by the shading. Where they meet at the transition portion 36, the shading has been omitted, because this is a portion where the materials of the three constituent elements flow into one another. Thus, it is indefinite where each of the constituent elements begin and end after molding. By comparison between FIGS. 4 and 5 it is evident that the leading parts 58, 60, and 62 blend into one matter, resulting in the transition portion 36. Preferably, the constituent elements of transition portion 36 are all polyurethane with the grades and sizes being chosen to provide the desired physical characteristics, such as a soft pliable tip section, a stiffer outer tube, and a thin-walled inner tube.

After the assembly has been molded as demonstrated in FIGS. 4 and 5, the tip section 38 is deformed in a conventional manner to create a tapered distal tip 72 on tip section 38 about the end opening 44. The combination of the tapered tip 72 and the transition portion 36 provides for a two-stage dilation of tissue of the patient as the distal end of catheter 20 is advanced along a Seldinger wire that extends through that tissue and has been disposed in return lumen 52 and through end opening 44.

The catheter 20 shown is typical of catheters that could be made in accordance with the invention. It is possible to proportion the tip portion 38 or provide soft material for the tip portion 38 so as to ensure that after insert through patient tissue the tip portion 38 will flex and will not damage blood vessels. At the same time, there is sufficient rigidity in the transition portion 36 to maintain the relationship between the tip portion 38 and the inner and outer tubes 48, 46, respectively, so that the intake lumen 50 remains patent while insertion takes place and during use. The arrangement is such that the lumen 50 is annular about the inner tube 48 right up to the intake opening 40, where the inner tube 48 is anchored in the transition portion 36 to ensure that all of the first side openings 40 lead to intake lumen 50.

Because the catheter 20 is normally entered over a wire and into an opening created by a dilator tip, the soft tip section 38 will not be required to cause major dilation. Consequently tip section 38 need only withstand the relatively small force needed to push the tip section 38 into the tissue of the patient. The final dilation takes place at the stronger transition portion 38 which can withstand the force needed to cause the final dilation of patient tissue to the size of the exterior of catheter 20.

It will be apparent that the structure can be varied within the scope of the invention. In particular, the tip section 38 need not be tapered, if insertion is through a sheath or by cut-down technique, and in such cases the distal end of the catheter could be closed. Also, the method of manufacture would be varied by extending the leading proximal part 60 further over the inner tube 48 to a point outside of mold 68, where leading proximal port 60 would not be affected by the forming of the transition portion 38. This unaffected end of part 60 would then naturally form the annular wall 70 without the need for the mandrel 64.

The proportions of the parts can be varied, and it would be possible to do some preforming before assembly. For instance, if desired, the tip portion 38 could be made larger with leading proximal part 60 thereof being deformed inwardly to fit inside the inner tube 46. Conversely, the inner tube 48 could be flared to fit around the tip section 38. Such variations are within the scope of the invention as described and claimed.

Figure 6:
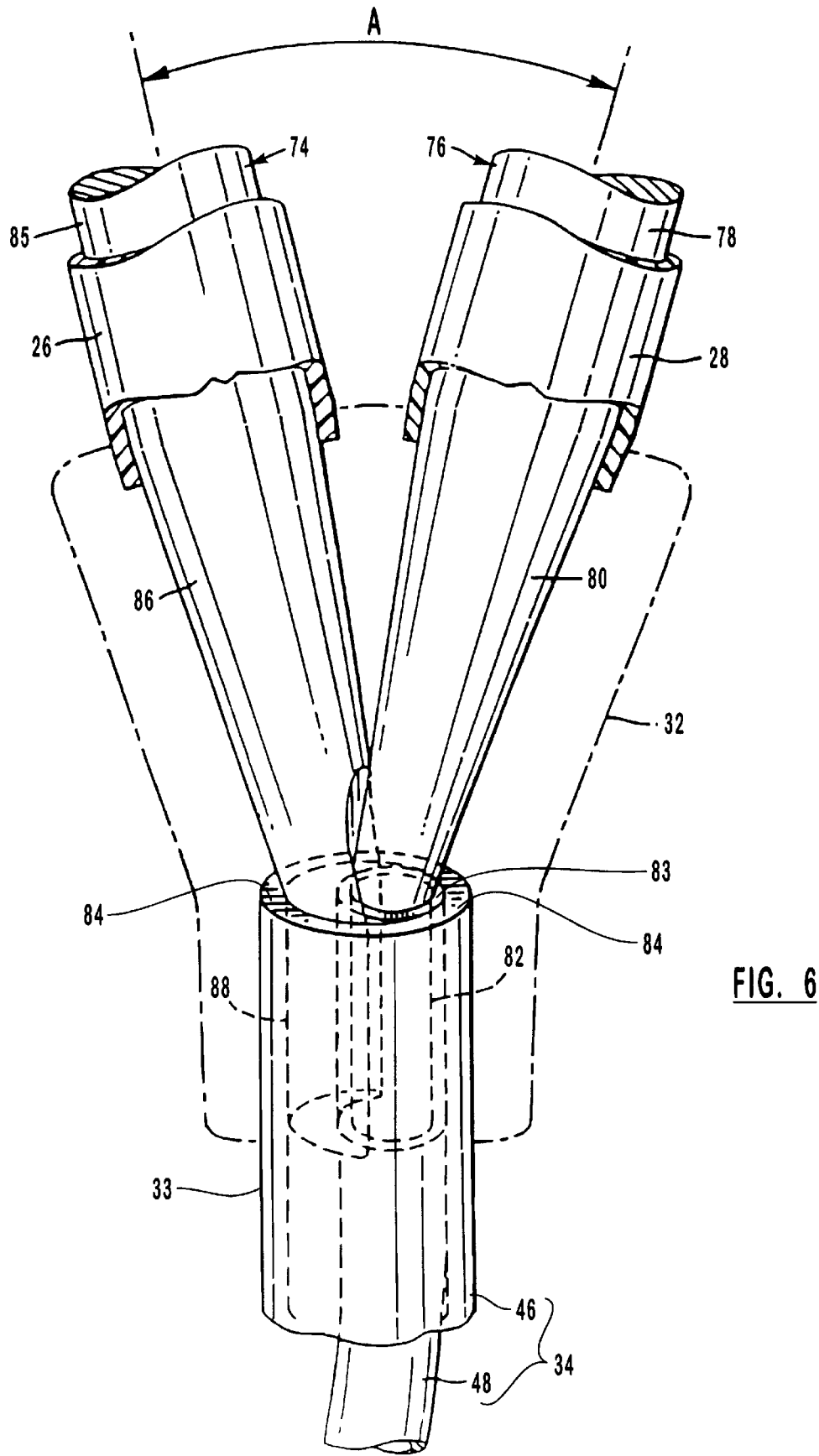
FIG. 6 is a perspective view in partial cross section of the junction at the proximal end of the catheter of FIG. 1 illustrating both the structure of the junction and a method of making the junction.

FIG. 6 illustrates the details of the junction 32, and in particular the method of manufacturing this junction. As seen in FIG. 6, the junction is prepared by first positioning proximal end 33 of the main catheter section 34 in a mold (not shown) which is to create in the recess therein the junction 32 by injection molding using conventional techniques. The main section 34 is positioned using first bent mandrel 74 and second bent mandrel 76. Second bent mandrel 76 has a proximal cylindrical portion 78 blending into a converging generally conical portion 80, which in turn blends into a distal cylindrical end part 82 that is angled with respect to the conical portion 80. End part 82 fits closely inside a proximal end 83 of the inner tube 48, which is maintained in a position in engagement with the inner surface of proximal end 85 of outer tube 46 by the mandrels 74, 76.

First bent mandrel 74 has a proximal cylindrical portion 85 which blends into a converging and generally conical portion 86 ending at a projection 88, which has a generally U-shaped configuration (as will be explained) and is angled with respect to the conical portion 86.

The projection 88 on the end of the mandrel 74 is shaped to fit the space provided inside proximal end 84 of outer tube 46, when inner tube 48 is held against the inner surface of the outer tube 46 by second bent mandrel 76. In transverse cross section, this space exhibits a generally U-shaped configuration. The angular offsets of the projection 88 and the distal cylindrical end part 82 of mandrel 76 result in the projection and end part 82 extending in parallel axially with respect to the main catheter section 34. The cylindrical portions 78 and 85 diverge sufficiently with respect to the longitudinal axis of main catheter section 34 so that the ends of access tubes 26, 28 can be accommodated on the mandrels.

Once the assembly shown in FIG. 6 has been completed, the mold is closed and injection takes place to form the junction 32. The material used is preferably polyurethane, although other materials can be used.

Mandrels 74, 76 are removed. Because there is flexibility in the material of which junction 32 is formed, the mandrels 74, 76 can be pulled out without causing any damage.

The structure shown in FIG. 6 has particular significance in the resulting flow through the catheter 20. Unlike previous coaxial catheters, the flow tend to remain linear due to the fact that access tubes 26, 28 are generally in line with the main catheter section 34. Previously, one of such access tubes was in line with the main catheter body section, while the second access tube was then necessarily connected through the side of the main catheter section. As a result, fluid flow through the second access tube was required to traverse a significant bend, which in some instances approached 90 degrees. This was most undesirable, because any changes in direction of this kind resulted in turbulence in the blood flow and a corresponding potential for damage to the blood. It is well established that pressure fluctuations in blood flow paths should be minimized, and this structure illustrated in FIG. 6 tends to limit such variations.

It is also significant that the resulting structure presents a smooth continuous internal surface to blood flow, which again is desirable.

The angle shown as "A" in FIG. 6 indicates the divergence between the access tubes 26, 28 at junction 32. Because of the construction method disclosed it is possible to maintain this angle in the order of 15 to 20 degrees and is readily maintained below 30 degrees. As a result, the flows into and out of the catheter 20 is essentially axial with reference to the main catheter section 34 at all times. This is because the angle of the tubes 26, 28 with reference to the axis of the main catheter section 34 is half of the range up to 30 degrees.

The embodiments described are representative of the invention and other embodiments and variations are within the scope of the invention as claimed.

I claim:

1. A dual lumen catheter comprising:
   a. an outer tube having a proximal end and a distal end;
   b. an inner tube having a proximal end and a distal end and defining therewithin a return lumen, said inner tube being smaller in outer cross-sectional area than the inner cross-sectional area of said outer tube, said inner tube being disposed within said outer tube to define between the outside of said inner tube and the inside of said outer tube an intake lumen having an annular cross section;
   c. a transition portion at said distal end of said inner tube and said distal end of said outer tube, said transition portion fixing said inner tube centrally within said outer tube to maintain said annular cross section of said intake lumen between said inner tube and said outer tube;

d. a junction containing said proximal ends of said outer tube and said inner tube, part of said inner tube adjacent said proximal end of said outer tube being positioned in contact with the inside wall of said outer tube, so that said intake lumen at said proximal end of said outer tube has a generally U-shaped cross section; and e. a first connecting tube and a second connecting tube engaged in said junction, said junction providing fluid continuity between said first connecting tube and said intake lumen and between said second connecting tube and said return lumen, thereafter permitting said catheter to be used for simultaneous dual flow.

2. A dual lumen catheter as recited in claim 1, wherein said first connecting tube and said second connecting tube each extend from said junction in a direction away from said inner tube and said outer tube with an angle of between 15 and 30 degrees between said first connecting tube and said second connecting tube.

3. A dual lumen catheter as recited in claim 1 further comprising:

a. an elongate tubular tip section extending longitudinally away from said transition portion to a distal end of said catheter, said tip section defining a return opening at the distal end of said tip section; and b. wherein said transition portion is formed of material provided in respective overlapping parts of said inner tube, said tip section, and said outer tube, said overlapping part of said tip section being engaged between said overlapping parts of said inner tube and said outer tube said overlapping part of said tip section and said overlapping parts of said outer tube and said inner tube blending smoothly into one another at said transition portion, said intake lumen ending at said transition portion, and said tip section forming an extension of said inner tube to extend said return lumen to said return opening at the distal end of said tip section.

4. A catheter as recited in claim 3, wherein said inner tube, said outer tubes and said tip section are round in cross section.

5. A catheter as recited in claim 4, wherein said tip section has an outside diameter greater than that of said inner tube and less than that of said outer tube.

6. A catheter as recited in claim 3, wherein said return opening is at said distal end of said catheter, and said tip section terminates at said distal end of said catheter in a tapered tip spaced longitudinally from said transition portion.

7. A catheter as recited in claim 3, wherein said tip section includes a side opening spaced proximally from said distal end of said catheter.

8. A catheter as recited in claim 4, wherein said outer tube has an outside diameter about twice that of said inner tube.

9. A catheter as recited in claim 3, wherein said outer tube includes a side opening spaced proximally from said transition portion, and the distal extent of said intake lumen at said transition portion.

10. A catheter as recited in claim 3, wherein said transition portion is tapered smoothly to converge from said outer tube to said tip section.

11. A catheter as recited in claim 3, wherein said tip section is more flexible than the remainder of said catheter.

12. A catheter as recited in claim 1, wherein said first connecting tube and said second connecting tube diverge at substantially equal angles to the longitudinal extent of said inner tube and of said outer tube.

13. A dual lumen catheter comprising:

a. an elongate body defining coaxial intake and return lumens;

b. a junction containing a proximal end of said elongate body with parts of said intake lumen and said return lumen in said junction constrained in side-by-side relationship; and c. a first connecting tube and a second connecting tube engaged in said junction and extending generally longitudinally away from said elongate body; said junction providing fluid continuity between said first connecting tube and said intake lumen, and between said second connecting tube and said return lumen, thereby permitting said catheter to be used for simultaneous dual flow.

14. A catheter as recited in claim 13, wherein said first connecting tube and said second connecting tube extend from said junction in a direction away from said elongate body at substantially equal angels to the longitudinal extent of said elongate body.

15. A dual lumen catheter as recited in claim 14, wherein said first connecting tube and said second connecting tube extend from said junction in a direction away from said elongate body at an angle of between 15 and 30 degrees between said first connecting tube and said second connecting tube.

16. A dual lumen catheter comprising:

a. an outer tube having a proximal end and a distal end;

b. an inner tube having a proximal end and a distal end and defining therewithin a return lumen, said inner tube being smaller in outer cross-sectional area than the inner cross-sectional area of said outer tube, said inner tube being disposed within said outer tube to define between the outside of said inner tube and the inside of said outer tube an intake lumen having an annular cross section; and c. a transition portion at which said distal end of said inner tube is nonremovably secured to said distal end of said outer tube, said transition portion comprising materials from each of said inner tube and said outer tube blended into an integral structure, said transition portion fixing said inner tube centrally within said outer tube to maintain said annular cross section of said intake lumen between said inner tube and said outer tube.

17. A dual lumen catheter as recited in claim 16, further comprising a junction comprising said proximal end of each of said inner tube and said outer tube, part of said inner tube adjacent said proximal end thereof being positioned in contact with the inside wall of said outer tube, so that said intake lumen at said proximal end of each of said inner tube and said outer tube has a generally U-shaped cross section.

18. A dual lumen catheter as recited in claim 17, wherein a first connecting tube and a second connecting tube are engaged in said junction, said junction providing fluid continuity between said first connecting tube and said intake lumen, and between said second connecting tube and said return lumen, thereafter permitting said catheter to be used for simultaneous dual flow.

19. A dual lumen catheter as recited in claim 16, further comprising:

a. an elongate tubular tip section of smaller cross section than said outer tube, the tip section having a return opening and extending longitudinally away from said transition portion to a distal end of said catheter, said tip section defining at least one return opening at the distal end of said tip section, and b. wherein said transition portion is formed of material provided in respective overlapping parts of said inner tube, said tip section, and said outer tube, said overlapping part of said tip section being engaged between said overlapping parts of said inner tube and said outer tube, said overlapping part of said tip section and said overlapping parts of said outer tube and said inner tube blending smoothly into one another at said transition portion, said intake lumen ending at said transition portion, and said tip section forming an extension of said inner tube to extend said return lumen to said return opening at the distal end of said tip section.

20. A catheter as recited in claim 19, wherein said inner tube, said outer tube, and said tip section are round in cross section.

* * * * *